United States Patent [19]

Gaudry et al.

[11] 3,950,511

[45] Apr. 13, 1976

[54] VACCINE FOR VIRAL PERICARDITE IN BARBARY DUCKS

[75] Inventors: Daniel Gaudry, Caluire; Pierre Precausta, Thurins, both of France

[73] Assignee: Institut Merieux, France

[22] Filed: Oct. 3, 1974

[21] Appl. No.: 511,710

[30] Foreign Application Priority Data

Oct. 5, 1973 France .............................. 73.35665

[52] U.S. Cl. ..................... 424/89; 195/1.1; 195/1.3
[51] Int. Cl.² ........................................ A61K 39/32
[58] Field of Search ................................... 424/89; 195/1.1–1.8

[56] References Cited
OTHER PUBLICATIONS

Gaudry et al., Comptes Rendus de L'Academie des Sciences, 274D(21):2919-2919, (1972), and Bulletin de la Societe des Sciences Veterinaires et de Medecine Comparee de Lyon, 74(2):137-143, (1972), "A Propos D'On Nouveau Virus Isole Chez Le Canard de Barbarie", Vet. Bull. 42(10), No. 5825, Oct. 1972.

Saint-Aubert et al., Bulletin de la Societe Dos Sciences Veterinaires et de Medecine Comparee de Lyon, 74(2):145-150, (1972), "A Propos D'un Cas De Pasteurellose A Pasteurellas Anatipesifer Chez Le Canard De Barbarie", Vet. Bull., 42(11), No. 6152, Nov. 1972.

Toth, Am. J. Vet. Res., 31:1275-1281, (1970), "Active Immunization of White Pekin Ducks Against Duck Virus Enteritis (Duck Plague) with Modified Live Virus Vaccine Immunization of Ducklings", Vet. Bull. 41, No. 663, (1971).

Toth, Am. J. Vet. Res., 32:75-81, (1971), "Active Immunization of White Pekin Ducks Against Duck Virus Enteritis (Duck Plague) with Modified Live Virus Vaccine: Serologic and Immunologic Response of Breeder Ducks", Vet. Bull., 41, No. 6292, (1971).

*Primary Examiner*—Shep K. Rose
*Attorney, Agent, or Firm*—Cushman, Darby & Cushman

[57] ABSTRACT

A vaccine against viral pericardite in Barbary ducks, also known as Carina Moschata or Muscovy ducks, comprises particles of "virus K" resulting from a succession of passages of said particles on embryo eggs or cells or both.

5 Claims, No Drawings

VACCINE FOR VIRAL PERICARDITE IN BARBARY DUCKS

The present invention relates to a vaccine against viral pericardite appearing in Barbary ducks, also known as Carina Moschata and Muscovy ducks, this disease being discussed in "Virologie — Une nouvelle affection se traduisant par une pericardite virale chez les canards de Barbarie" Compte Rendus, Acad. Sc. Paris, t. 274, p. 2916–2919 Serie D May 24, 1972, by MM Daniel Gaudry, Jean-Marie Charles and Jacques Tektoff; "A propos d'un nouveau virus isolé chez le canard de Barbarie", Daniel Gaudry, Jacques Tetkoff and Jean-Marie Charles, Bull. Soc. Sci. Vet. et Med. comparée, Lyon 1972, 74; and "A propos d'un cas de Pasteurellose à Pasteurella anatipestifer chez le canard de Barbarie", G. de Saint-Aubert, J. M. Charles and D. Gaudry, Bull. Soc. Sci. Vet et Med. comparée, Lyon, 1972, 74.

This disease has been attributed to a new virus called "virus K", probably running from the reovirus.

The disease resulting from this virus is manifested frequently by the destruction of commerical breeding of Barbary ducks, so that intensive breeding of this duck is actually very uncertain or hazardous.

The invention proposes to remedy this disadvantage by furnishing a vaccine capable of effectively protecting these ducks against the above stated disease.

The vaccine according to the present invention exhibits no toxicity toward Barbary ducks and provides practically complete immunity against "virus K" for these ducks.

The present invention thus has for an object a vaccine against viral pericardite in Barbary ducks due to "virus K", characterized by the fact that it contains viral particles of "virus K" having undergone a plurality of passages on eggs or on cells.

The vaccine according to this invention is preferably present in lyophilized form. While an adjuvant can be included, its presence is not necessary.

Preferably, the vaccine comprises a living vaccine but as a variation of the present invention, the vaccine can be inactivated using a conventional inactivating agent such as formol or ultra-violet radiation.

The invention also has for an object a process for the preparation of this vaccine, characterized by the fact that one adapts "virus K" on embryo eggs or embryo cells.

In a preferred embodiment, the virus first undergoes 20 passages on embryo Barbary duck eggs, followed by 30 passages on embryo chicken eggs following which it undergoes 30 passages on embryo chicken cells. The cells and the culture medium are then collected, mixed together with a lyophilization stabilizer and then lyophilized.

In another embodiment of the present invention, the virus first undergoes 20 passages on embryo Barbary duck cells, then about 55 passages on embryo chicken cells, following which the cells and the culture medium are collected and then lyophilized.

Vaccination is effected on young Barbary ducks by subcutaneous injection, the average dosage being preferably between 0.5–1 ml. The dosage comprises between 100–10,000 TCID (tissue culture infectious doses).

Other advantages and characteristics of the invention will appear from a reading of the following non-limiting description.

The source virus is obtained from ducks having a viral disease caused by "virus K". This is effected by grinding the liver and spleen of the ducks, the resulting ground mass then being centrifuged. The supernatant liquid, first diluted, is then filtered on a Millepore membrane to provide a viral suspension which then undergoes 20 passages on embryo Barbary duck eggs at a temperature between 37°–39.5°C. The average duration of each passage is 10 days.

Following the 20th passage, the suspension then undergoes 30 passages on embryo chicken eggs at a temperature of preferably between 37°–39.5°C.

Using the embryonic liquid recovered after the 30th passage on the embryo chicken eggs, a cell culture of embryo chicken, cultivated at a temperature between 37° and 39.5°C is infected with a $F_{10}$ - 199 medium (Agriculture Research Service U.S.D.A. — Agriculture Handbook 404–1971, 1–18). The embryonic liquid then undergoes 30 passages on the cells and after the 30th passage, the cells as well as the culture medium are collected.

The resulting mass is then admixed with a lyophilization stabilizer such as sucrose and with a phosphate buffer and then lyophilized in a conventional fashion. The resulting lyophilized vaccine is capable of being taken up in physiologic water for administration.

Although the invention has been described relative to a particular embodiment, it is to be understood that the invention is not limited thereto and various modifications can be made without departing from the spirit or scope of the invention.

What is claimed is:

1. A vaccine against viral pericarditis in Barbary ducks comprising a vehicle containing particles of "virus K" reovirus resulting from source virus obtained from the liver and spleen of Barbary ducks having a viral disease caused by Barbary duck viral pericardite "virus K" reovirus, said source virus having then undergone (a) 20 passages on embryo Barbary duck eggs, then 30 passages on embryo chicken eggs, followed by 30 passages on embryo chicken cells or (b) 20 passages on embryo Barbary duck cells, followed by about 55 passages on embryo chicken cells.

2. The vaccine of claim 1 in the form of unit doses comprising between $10^2$ and $10^4$ TCID.

3. The vaccine of claim 1 in lyophilized form.

4. The vaccine of claim 1 in lyophilized form obtained by admixing said vaccine with sucrose and with a phosphate buffer and lyophilizing the resulting mixture.

5. A method of vaccinating a young Barbary duck which comprises subcutaneously injecting said duck with a unit dose of the vaccine of claim 1, said unit dose of said vaccine comprising between $10^2$ and $10^4$ TCID.

* * * * *